United States Patent [19]
McKeever

[11] Patent Number: 5,683,363
[45] Date of Patent: Nov. 4, 1997

[54] BALLOON PUMP ANGIOPLASTY SYSTEM AND METHOD OF USE

[76] Inventor: Louis Stephen McKeever, 312 Blackstone, LaGrange, Ill. 60525

[21] Appl. No.: 723,618

[22] Filed: Oct. 2, 1996

Related U.S. Application Data

[62] Division of Ser. No. 434,564, May 4, 1995, Pat. No. 5,613,946.

[51] Int. Cl.⁶ ................................................. A61M 29/00
[52] U.S. Cl. ................................................. 604/96; 604/49
[58] Field of Search .................................. 604/96, 101, 102, 604/49–53, 280–283, 192, 193, 194

[56] References Cited

U.S. PATENT DOCUMENTS

| | | | |
|---|---|---|---|
| 5,226,889 | 7/1993 | Sheiban | 604/96 |
| 5,320,605 | 6/1994 | Sahota | 604/96 |
| 5,516,336 | 5/1996 | McInnes et al. | 604/96 X |
| 5,533,968 | 7/1996 | Moni et al. | 604/102 X |

*Primary Examiner*—John D. Yasko
*Attorney, Agent, or Firm*—Niro, Scavone, Haller & Niro

[57] ABSTRACT

Devices and methods for simultaneously performing mechanical circulatory assistance and percutaneous transluminal coronary angioplasty ("PTCA") during periods of hemodynamic instability through a single femoral puncture site. One embodiment includes a balloon pump catheter that includes a lumen that communicates with a balloon located at the distal end of the catheter and a second lumen which has been proportionally sized to receive a coronary angioplasty guiding catheter which is insertable into the lumen. Once the balloon pump catheter is in place and operational, the guiding catheter is further advanced towards the coronary ostium where it then receives an angioplasty balloon catheter that is used to perform angioplasty for the removal of the blockage.

In another embodiment of the present invention, the intra aortic balloon pump catheter is releasingly connected to an angioplasty guiding catheter which allows for the simultaneous insertion of both catheters. Once the balloon pump catheter is in place and operational, the guiding catheter is further advanced to a point where an angioplasty balloon catheter can then be inserted for the removal of the blockage.

9 Claims, 6 Drawing Sheets

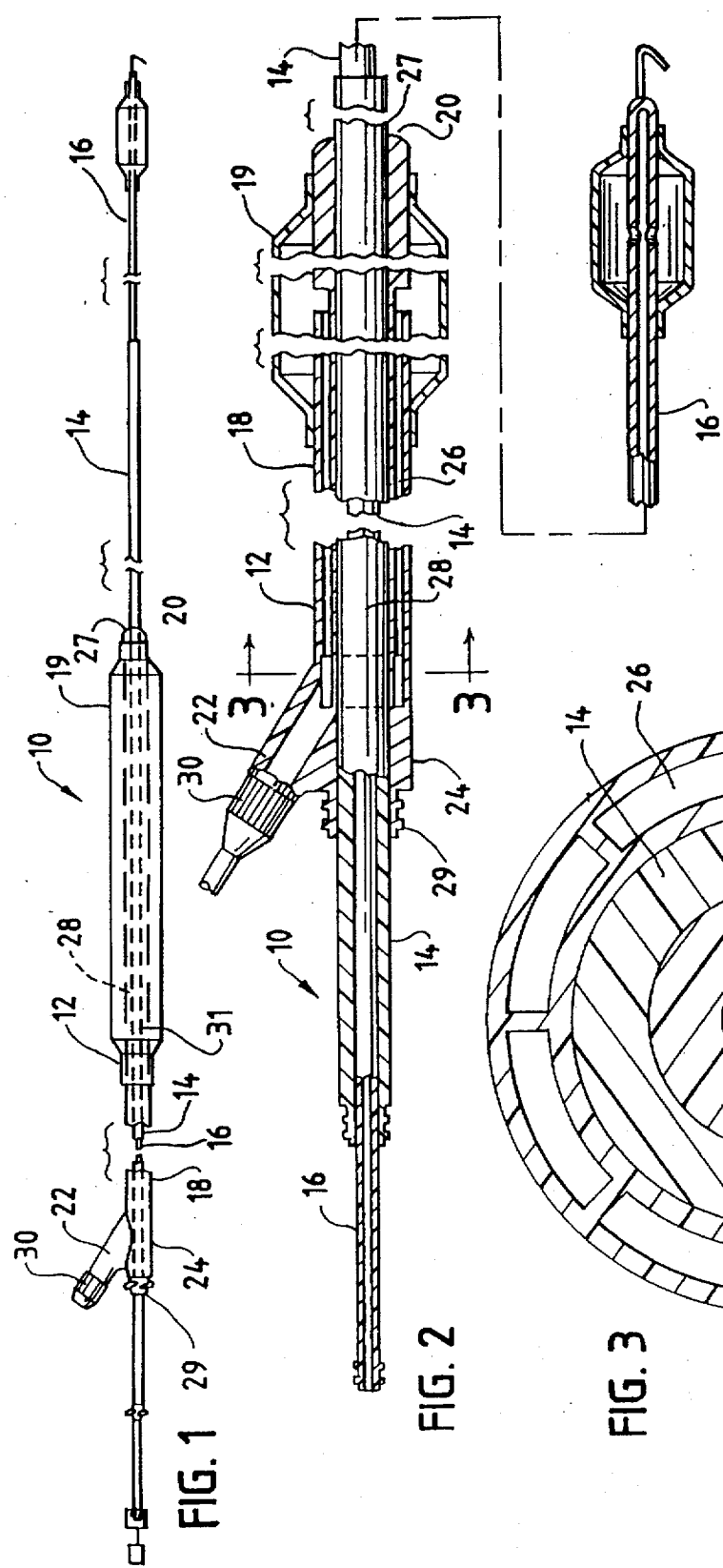
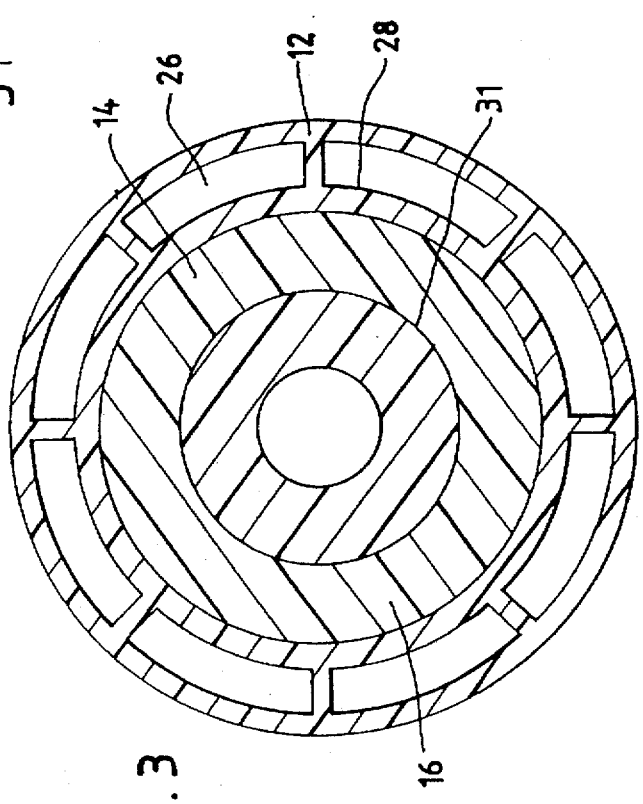
FIG. 1
FIG. 2
FIG. 3

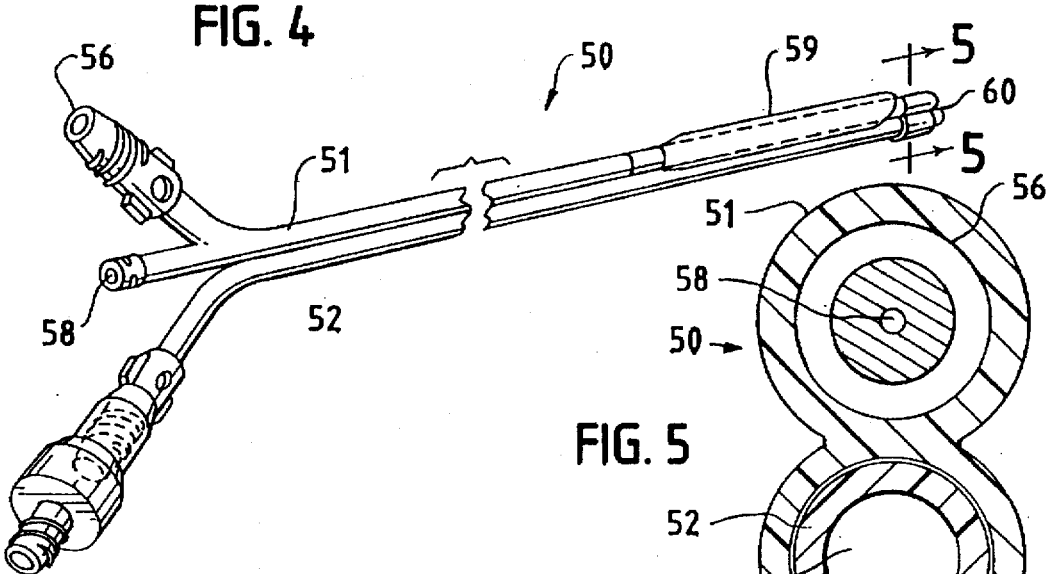
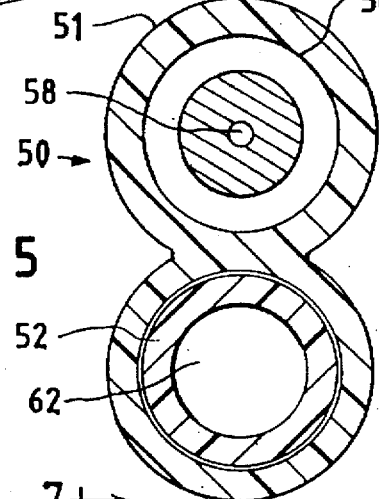
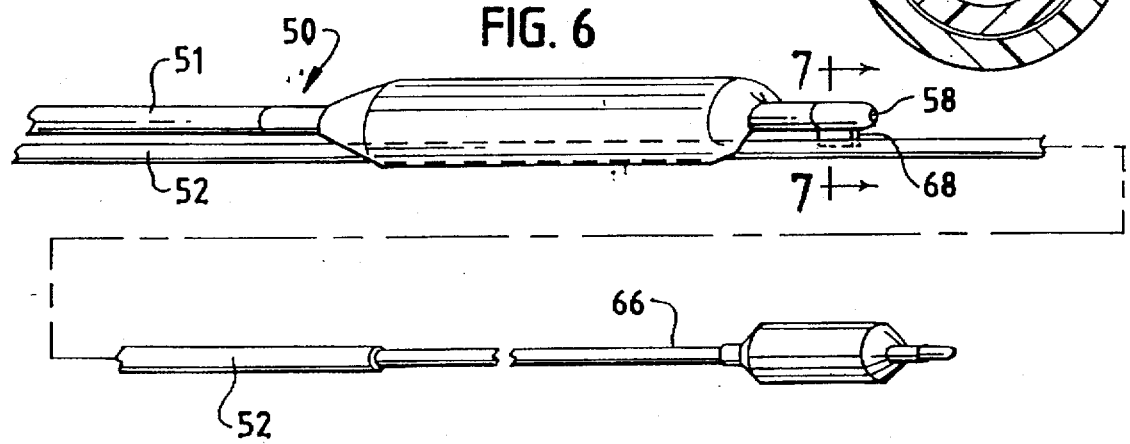
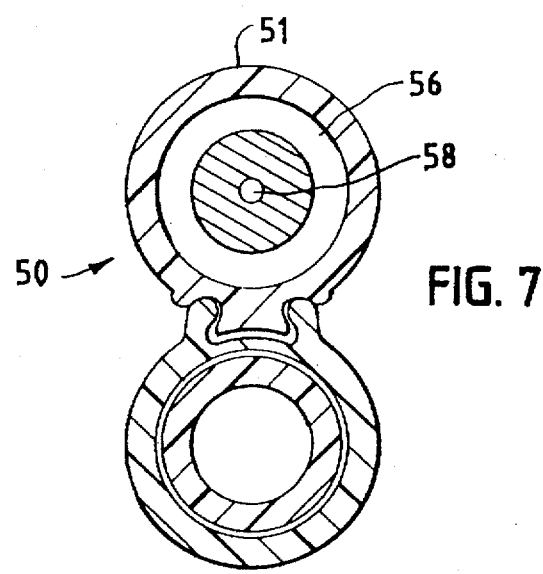

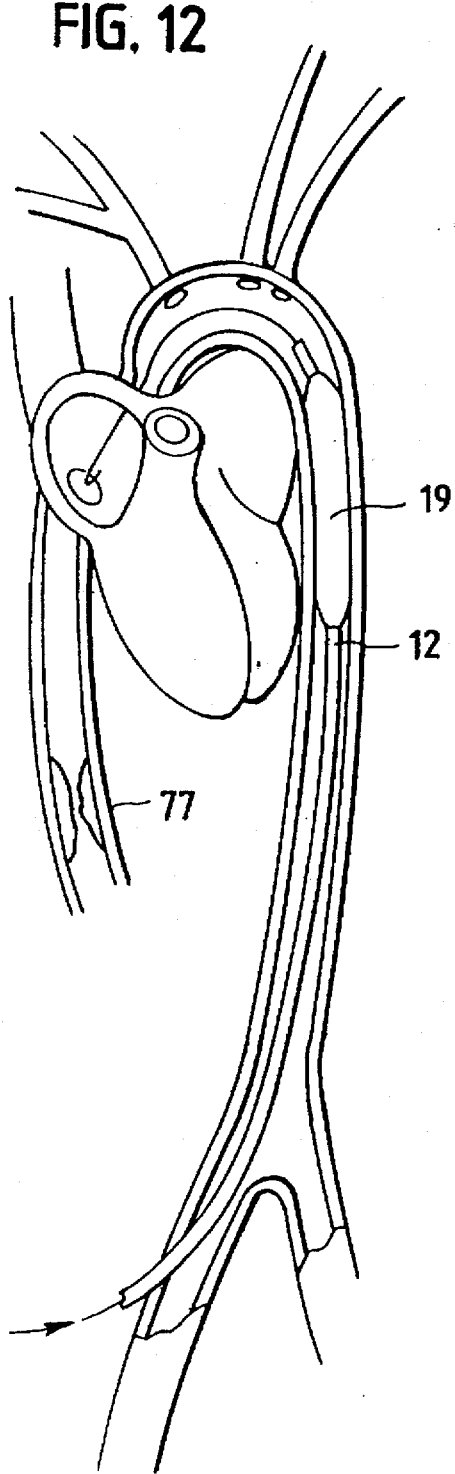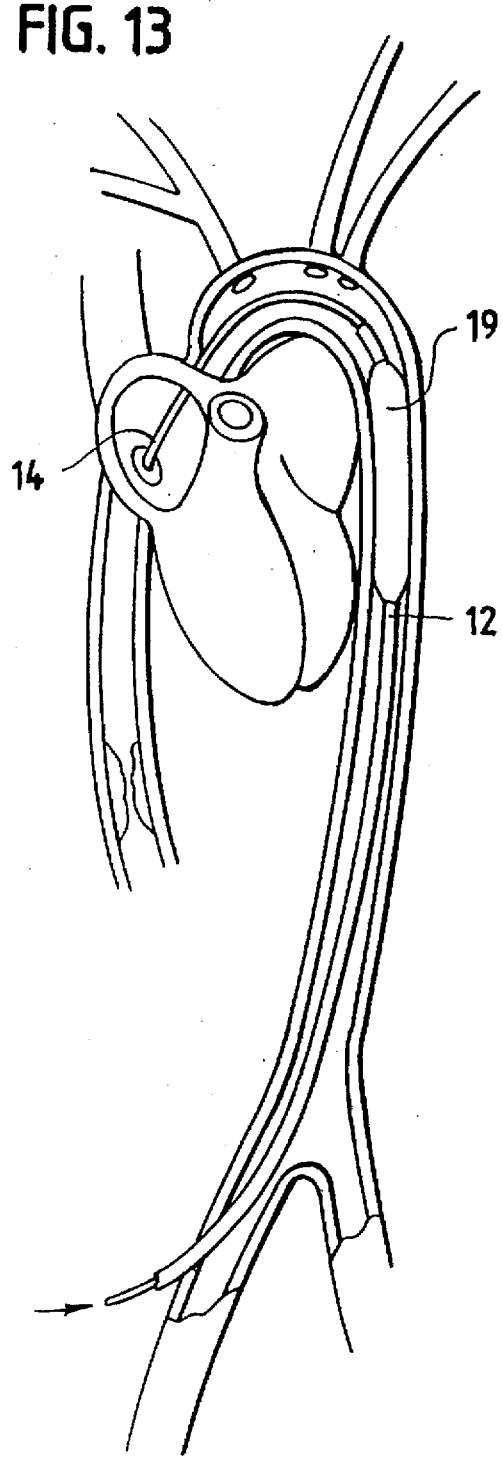

FIG. 14
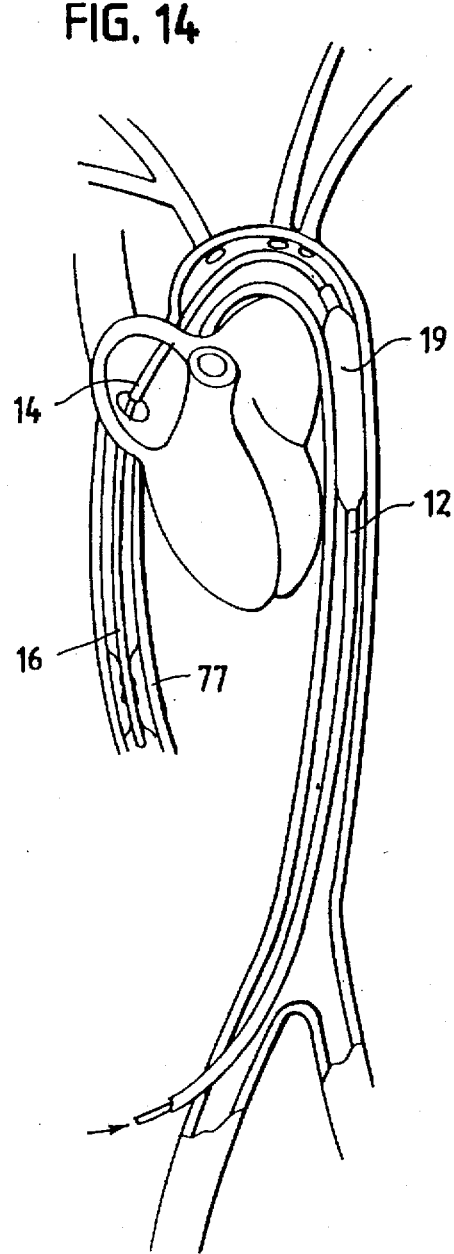
FIG. 15
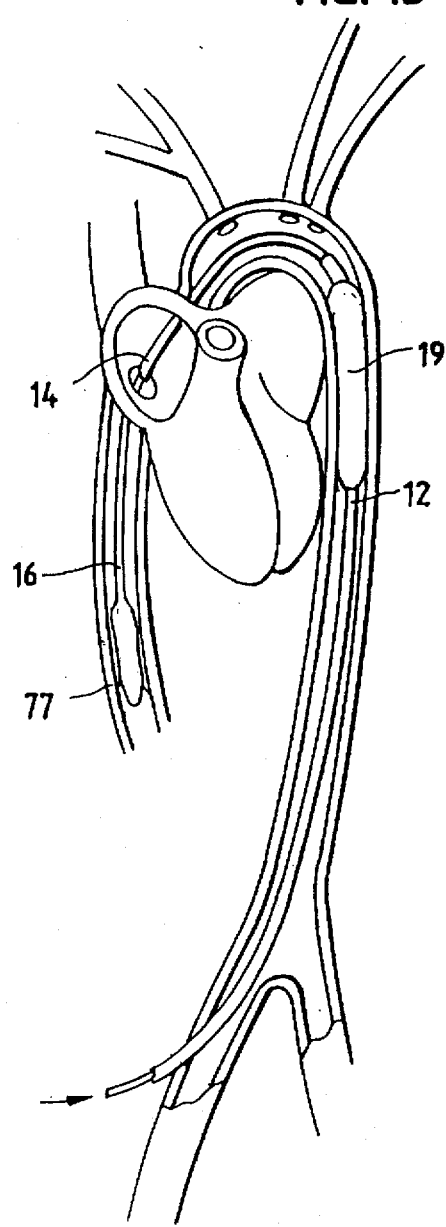
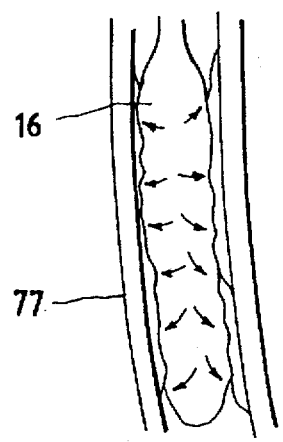
FIG. 16

BALLOON PUMP ANGIOPLASTY SYSTEM AND METHOD OF USE

This is a divisional application Ser. No. 08/434,564 filed on May 4, 1995 now U.S. Pat. No. 5,613,946.

BACKGROUND OF THE INVENTION

The present invention relates to a method and apparatus which is used to simultaneously perform mechanical circulatory assistance and percutaneous transluminal coronary angioplasty ("PTCA") during periods of hemodynamic instability through a single femoral puncture site. More particularly, the invention consists of a intra aortic balloon pump catheter ("IABP") that is capable of receiving a coronary angioplasty guiding catheter, which in turn, receives and guides an angioplasty balloon catheter for performing PTCA.

Historically, often during periods of hemodynamic crises, a patient will typically require immediate coronary intervention through PTCA in order to remove the coronary blockage. In addition, to decrease the risk of the angioplasty procedure, simultaneous use of an IABP stabilizes the hemodynamic instability by providing augmented diastolic pressure. Moreover, recent medical data suggests that continued use of the IABP after PTCA will decrease the abrupt closure rate.

However, the present state of the art is such that both procedures (IABP and PTCA) typically need to be performed at the same femoral puncture site. For example, to place and operate an IABP, the common practice is to first gain access to the circulatory system at either the right or left femoral artery and to then work the IABP up to the descending thoracic aorta just distal to the left subclavian artery where it is then operated. Similarly, when performing PTCA, the common practice is to also first gain access for an angioplasty guiding catheter at either the right or left femoral artery and to then work the guiding catheter up to the appropriate coronary ostium. Once the guiding catheter is properly positioned, an angioplasty balloon catheter is then inserted into a lumen of the guiding catheter and positioned at the stenosis for the removal of the blockage.

This competition for the same femoral access site leads to difficulties in performing both operations simultaneously, since once an IABP is placed at a femoral site, no other intervention, such as PTCA, can be performed at that puncture site. Because of this limitation, practitioners must often chose to perform one procedure first, depending upon the situation, and then follow with the other procedure afterwards.

Alternatively, both procedures have been performed by using two operators. This is done by having one operator perform PTCA at one femoral puncture site, while another operator is placing an IABP at the opposing femoral puncture site. However, this type of procedure is not always an option due to the availability of practitioners or the blockage of one of the femoral sites.

SUMMARY OF THE INVENTION

The present invention preserves the advantages of simultaneously using an IABP while performing PTCA. Specifically, the invention overcomes the above mentioned disadvantages by providing an balloon pump angioplasty system having an IABP that is adapted to receive a coronary angioplasty guiding catheter which is used, in turn, for the placement and operation of an angioplasty balloon catheter.

In one embodiment of the present invention, the IABP contains at least two lumens which may be either coaxially or eccentrically disposed. One lumen communicates with a balloon portion distally located on the IABP and the other lumen is sized to accept and receive a corresponding coronary angioplasty guiding catheter which is insertable into and through the lumen. The guiding catheter, in turn, contains a guiding lumen which receives and assists in the placement and operation of an angioplasty balloon catheter which is used to remove the stenosis. This advantageous combination of catheters allows for the simultaneous use of IABP and PTCA at a single femoral site.

In another embodiment of the present invention, the coronary angioplasty guiding catheter and IABP are releasingly connected together. This produces a system having a generally elliptical cross-section which allows the IABP and guiding catheter to be simultaneously inserted as a single piece. Once the IABP is positioned, the releasable connection then allows the guiding catheter to be further advanced towards the coronary ostium. Once the guiding catheter is positioned, an angioplasty balloon catheter is inserted and placed for the removal of the stenosis as was generally described above. The advantage of the generally elliptical cross-section is that it provides an increased working diameter without unnecessarily expanding the device's circumference.

Not only does the present invention provide a single practitioner with the flexibility and adaptability needed to simultaneously place and use an IABP and perform PTCA, the invention offers the patient a number of safety benefits as well. First, the present invention requires no delay in performing PTCA or IABP while gaining arterial access. Second, the invention is more efficient in emergency situations since it only requires one operator and one femoral puncture site. Lastly, simultaneous PTCA and IABP can be performed even if only one femoral puncture site is available.

Accordingly, an object of the present invention is to provide a balloon pump angioplasty system and method of using the same which is more flexible, safer and easier to use than present IABP and angioplasty guiding catheters and methods.

Another object of the present invention is to provide a balloon pump angioplasty system and method which overcomes the need to use two operators and two femoral puncture sites in order to perform simultaneous PTCA and IABP.

A further object of the present invention is to provide a balloon pump angioplasty system and method which is more efficient to use in emergency conditions.

BRIEF DESCRIPTION OF THE DRAWINGS

These and other features, objects and advantages of the present invention will become apparent from the following description and drawings wherein like reference numerals represent like elements in the several views, and in which:

FIG. 1 is a perspective view of one embodiment of the invention;

FIG. 2 is an enlarged, length-wise cross sectional view of the embodiment shown in FIG. 1;

FIG. 3 is a view in section of the embodiment illustrated in FIG. 2 taken along line 3—3;

FIG. 4 is a perspective view of another embodiment of the invention;

FIG. 5 is a view in section of the embodiment illustrated in FIG. 4 taken along line 5—5;

FIG. 6 is an enlarged perspective view of a portion of the embodiment shown in FIG. 4;

FIG. 7 is a view in section of the embodiment illustrated in FIG. 5 taken along line 7—7;

FIGS. 8–15 are perspective views depicting the placement and operation of the invention in the circulatory system for the removal of a stenosis; and FIG. 16 is an enlarged pictorial showing the removal of a stenosis through angioplasty.

DETAILED DESCRIPTION OF THE PREFERRED EMBODIMENTS

Figure 8:
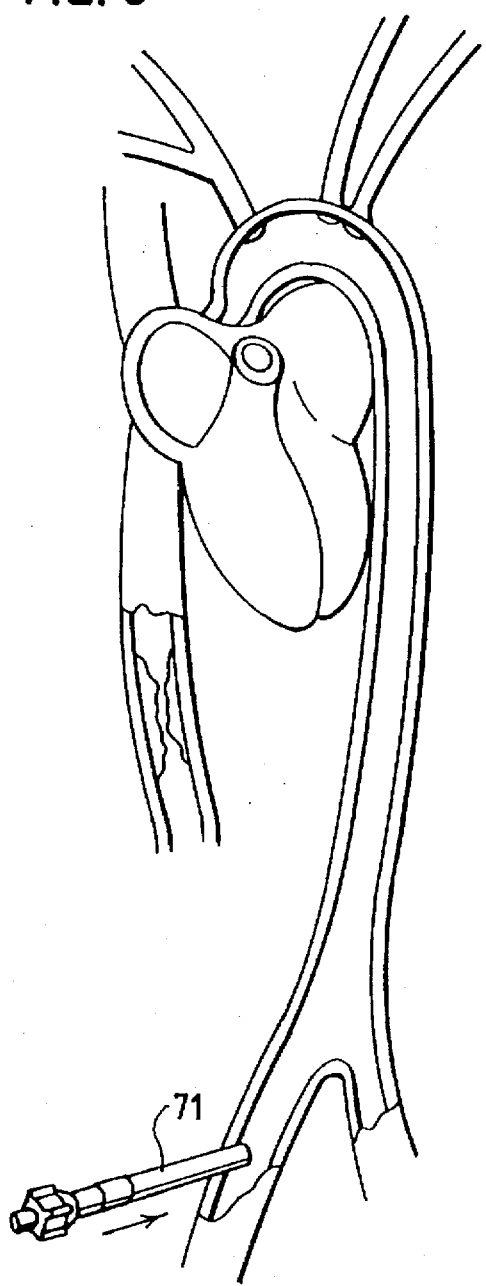

FIG. 1 shows a balloon pump angioplasty catheter system 10 consisting of an intra aortic balloon pump catheter 12, coronary angioplasty guiding catheter 14, and angioplasty balloon catheter 16. As shown in FIGS. 1 and 2, balloon pump catheter 12 has an elongated tube 18 with an inflatable balloon portion 19 located at distal end 20 and branching connector 22 located at proximal end 24. As with other similar devices, polymers such as PVC (polyvinylchloride) and various derivatives of polyethylene have proven to be suitable for making coronary balloon catheters. Others of ordinary skill in the art would also recognize that other bio-compatible materials, such as Mylar, may also be used.

As illustrated in FIG. 3, balloon catheter 12 further includes at least two lumens 26 and 28 which may be either coaxially (shown) or eccentrically (not shown) disposed or configured in other ways familiar to those of ordinary skill in the art. Outer lumen 26 communicates with balloon 19 and is connected to a pump (not shown) by inlet line 30. Lumen 28 is generally an axial bore which runs along the entire length of tube 18 from luer hub 29 located at proximal end 24 to aperture 27 located at distal end 20.

Lumen 28 receives and guides a guide wire (not shown) which is used to insert and place catheter 12. Lumen 28 also receives and guides angioplasty guiding catheter 14 which is inserted into lumen 28 at hub 29 and completely through lumen 28 at aperture 27.

To accommodate angioplasty guiding catheter 14, the diameter of lumen 28 needs to be proportionally related to the outer diameter of catheter 14. Since the outer diameter of currently available angioplasty guiding catheters is between 6 to 8 French, the diameter of lumen 28 should be proportionally sized to accommodate and accept catheter 14. Coating lumen 28 with a hydrophilic substance will further promote ease of insertion. To minimize the insertion trauma of the entire device, the outer diameter of catheter 12 should not exceed 11 French.

Catheter 14 is of a construction which is similar to currently available coronary angioplasty guiding catheters. Catheter 14 preferably includes at least one guide lumen 31, a luer locking hub 32 located at proximal end 34 and a radio opaque tip 36 and aperture 37 located at distal end 38 for the tracking of the catheter by a fluoroscopy. In addition, to promote placement of distal end 38 and tip 36 into the coronary, distal end 38 may contain a slight bend (not shown) which assists in the placement of the catheter.

Since catheter 14 is intended to be insertable into lumen 28 of catheter 12, the outer diameter of catheter 14 should be in a range of 6 to 8 French. To aid in the insertion of the entire system, a smaller outer diameter size is preferable since use of the smaller size allows the overall diameter of the device to be less. Moreover, in order for guide lumen 31 to accept and receive currently available angioplasty balloon catheters, its diameter should be in the range of about 0.035 inch.

To complete the system, an angioplasty balloon catheter 16 is provided. Catheter 16 is of design which is widely available by manufacturers such Advanced Cardiovascular Systems or Boston Scientific.

An alternate embodiment of the invention is shown in FIGS. 4–7 and is generally designated as combined catheter 50. This embodiment uses an intra aortic balloon pump catheter 51 that has been adapted to be releasingly connected to guiding catheter 52. Catheter 51 is of the same general construction as was described above for catheter 12 and, as shown in FIGS. 4–7, catheter 51 includes lumen 56 which communicates with balloon 59 and another lumen 58 which is used in connection with a guide wire (not shown) for the placement of catheter 50. Distally located on catheter 51 is retainer 60 which connects catheters 51 and 52 together in a releasable relationship. As shown in FIGS. 4 and 5, retainer 60 can be a retaining clip that has been attached to the device or molded directly into catheter 51. Alternately, as shown in FIGS. 6 and 7, the catheters may be connected through the use of tongue 63 and groove 65 channels 68 as well as other keyed or mated surfaces and the like. Of course, these and other methods to releasingly connect the catheters known to persons of ordinary skill art would be within the scope of the invention.

As will be explained more fully below, during insertion catheters 51 and 52 remain secured together. However, once catheter 51 is properly positioned and operational, catheter 52 will require further advancement into the circulatory system. The releasable connection between the two catheters permits the further positioning of catheter 52.

As shown in FIGS. 5 and 7, catheter 50 has a generally elliptical cross-section. Such a cross-section is advantageous since it provides an increased working diameter without unnecessarily expanding the device's circumference.

Catheter 52 is of the same design and construction as guiding catheter 14 and includes a lumen 62 which is designed to accommodate an angioplasty balloon catheter 66. Catheter 66 is of a similar design as was described above.

In use, an arterial puncture of either the right or left femoral artery is first made as shown in FIG. 8 for either embodiment. Then, using a Seldinger Technique, a femoral artery access is achieved with placement of an appropriate size sheath 71 that will accept balloon pump angioplasty catheter 12 or catheter 50. Once access is achieved, the devices are prepared in the usual manner with a negative prep before insertion.

To aid in the initial insertion, a styler measuring 6 or 7 French may be used in order to maintain stiffness of the catheter. Alternatively, in the embodiment shown in FIG. 1, angioplasty guiding catheter 14 may be inserted within lumen 28 before the placement of the catheter.

Figure 9:
Figure 10:
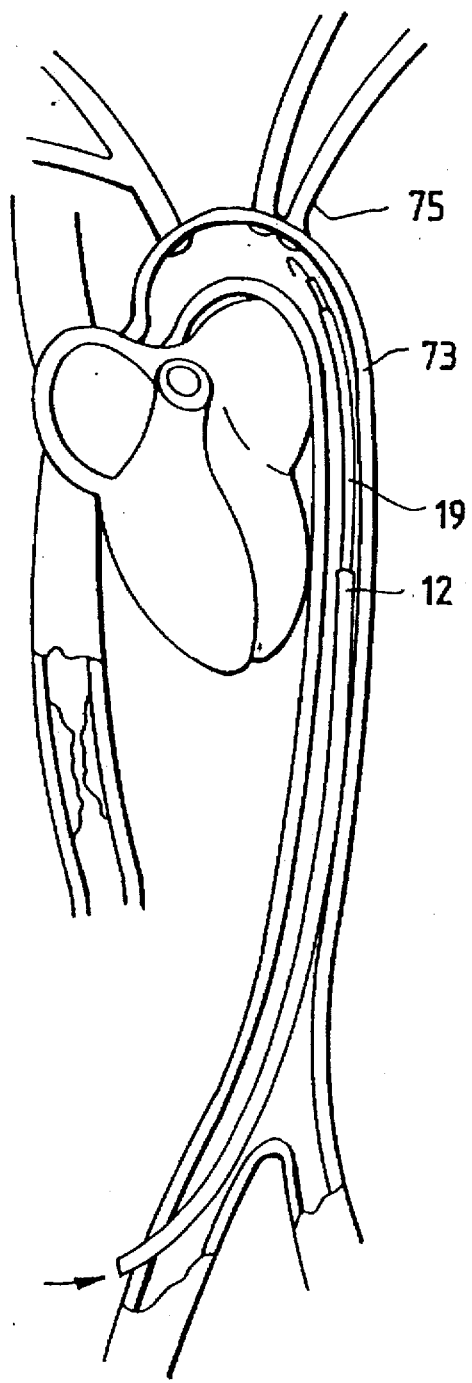
Figure 11:
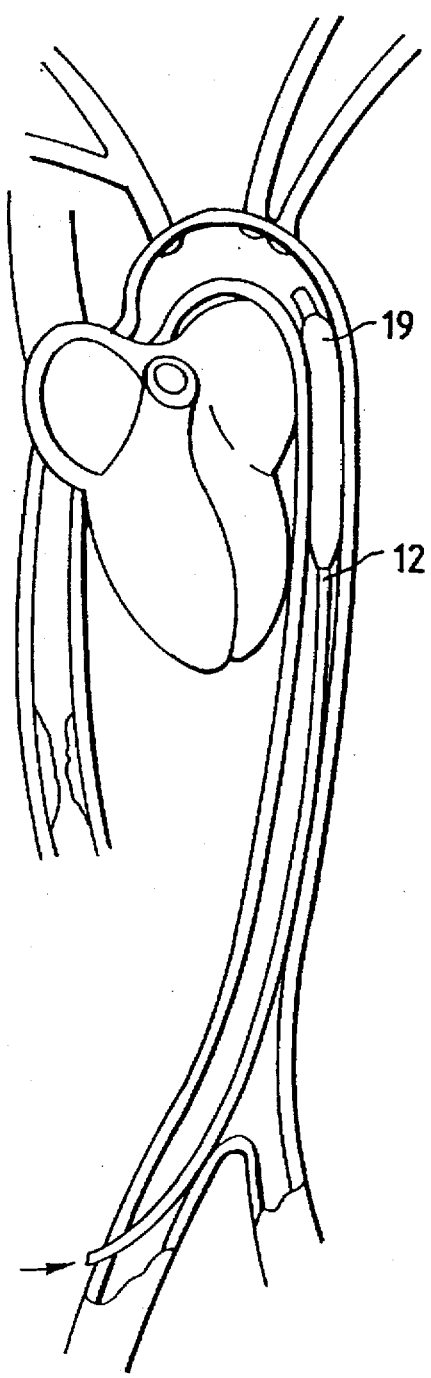

As shown in FIG. 9, a guide-wire 70 is first advanced around the arch of the aorta 72. As shown in FIG. 9, catheter 12 or combined catheter 50 are then tracked over the guide-wire and positioned in the descending thoracic aorta 73 just distal to the left subclavian artery 75. Once in position, intra aortic balloon pump catheter 12 or 51 is then connected to a balloon pump machine and pumping is begun immediately.

For the embodiment shown in FIGS. 1–3 and as shown in FIGS. 12–15, guiding catheter 14 is then inserted into and through lumen 28 and advanced to the coronary ostium 77. Coronary angioplasty is then performed in the usual manner by the insertion and use of angioplasty balloon 16.

For the embodiment shown in FIGS. 4–6, guiding catheter 52 and IABP catheter 51 are simultaneously advanced together over a guide wire until the IABP is properly placed and operational. Guide catheter 52, which is releasably connected to catheter 51, is then advanced further into the circulatory system until properly positioned at the coronary ostium. Once positioned, coronary angioplasty is then performed in the usual manner by the insertion and use of angioplasty balloon 66.

For both embodiments, balloon pumping continues throughout the angioplasty. At the end of the angioplasty, angioplasty balloon catheter 16 or 66 and guiding catheter 14 or 52 are then removed and replaced by a styler. The intra aortic balloon pump catheter 12 or 51 is then sutured in place and the use of the IABP is continued for as long as desired.

While the preferred embodiments of the present invention have been illustrated and described, it will be understood by those of ordinary skill in the art that changes and other modifications can be made without departing from the invention in its broader aspects.

What is claimed is:

1. A balloon pump angioplasty system to be used at a single femoral puncture site comprising:

an intra aortic balloon pump catheter consisting of a tube having a proximal and distal end, at least two lumens disposed within said tube, and an expandable balloon portion located at said distal end of said tube;

said first lumen in communication with said balloon;

said second lumen is an axial bore which runs from said proximal end of said tube to said distal end of said tube where it terminates in an aperture;

said second lumen is proportionally sized to receive a coronary angioplasty guiding catheter which is insertable into and through said second lumen;

said coronary angioplasty guiding catheter including a guiding lumen running through the entire length of said guiding catheter which terminates in an aperture; and an angioplasty balloon catheter insertable into and through said guiding lumen whereby percutaneous transluminal coronary angioplasty may be simultaneously performed along with the use of an intra aortic balloon pump catheter at said single femoral puncture site.

2. The device of claim 1 wherein the diameter of said second lumen is in the range of about 6–8 French.

3. The device of claim 1 wherein the diameter of said guiding lumen is approximately 0.035 inch.

4. The device of claim 1 wherein said lumens are coaxially disposed.

5. The device of claim 1 wherein at least one of said lumens is eccentrically disposed with respect to the other of said lumens.

6. A method for performing percutaneous transluminal coronary angioplasty along with use of a intra aortic balloon pump catheter at a single femoral puncture site, comprising the steps of:

inserting into a preselected femoral artery an intra aortic balloon pump catheter consisting of a tube having a proximal end, a distal end, and at least two lumens, one of which is in communication with a distally located balloon;

operating said intra aortic balloon pump catheter after said balloon pump is positioned in the descending thoracic aorta just distal to the left subclavian artery by connecting one of said lumens to a balloon pump machine;

inserting into and through the other of said lumens of said balloon pump a coronary angioplasty guiding catheter having a guiding lumen running through the entire length of said guiding catheter which terminates in an aperture; and inserting into and through said guiding lumen an angioplasty balloon catheter whereby percutaneous transluminal coronary angioplasty may be simultaneously performed along with the operation of said intra aortic balloon pump catheter at a single femoral puncture site.

7. The method of claim 6 wherein said intra aortic balloon pump catheter further includes a third lumen used in connection with a guide wire.

8. The method of claim 6 wherein said intra aortic balloon pump catheter contains at least two coaxially disposed lumens.

9. The method of claim 6 wherein said intra aortic balloon pump catheter contains at least one eccentrically disposed lumen.

* * * * *